(12) United States Patent
Biberger

(10) Patent No.: US 8,945,219 B1
(45) Date of Patent: Feb. 3, 2015

(54) SYSTEM FOR AND METHOD OF INTRODUCING ADDITIVES TO BIOLOGICAL MATERIALS USING SUPERCRITICAL FLUIDS

(75) Inventor: Maximilian A. Biberger, Scottsdale, AZ (US)

(73) Assignee: SDCmaterials, Inc., Tempe, AZ (US)

( * ) Notice: Subject to any disclaimer, the term of this patent is extended or adjusted under 35 U.S.C. 154(b) by 1288 days.

(21) Appl. No.: 12/151,841

(22) Filed: May 8, 2008

Related U.S. Application Data

(60) Provisional application No. 60/928,946, filed on May 11, 2007.

(51) Int. Cl.
*A61F 2/28* (2006.01)
*A61F 2/54* (2006.01)

(52) U.S. Cl.
USPC ................................. 623/16; 623/66

(58) Field of Classification Search
USPC ........................................ 623/16, 66
See application file for complete search history.

(56) References Cited

U.S. PATENT DOCUMENTS

| | | | |
|---|---|---|---|
| 5,725,579 | A | 3/1998 | Fages et al. |
| 6,149,864 | A | 11/2000 | Dillow et al. |
| 7,008,591 | B2 | 3/2006 | Kafesjian et al. |
| 7,550,152 | B2 | 6/2009 | Pandit et al. |
| 8,007,718 | B1 * | 8/2011 | Biberger ................ 422/28 |
| 2003/0027125 | A1 | 2/2003 | Mills et al. |
| 2003/0066800 | A1 | 4/2003 | Saim et al. |
| 2003/0072677 | A1 | 4/2003 | Kafesjian et al. |
| 2004/0020518 | A1 | 2/2004 | DeYoung et al. |
| 2004/0023453 | A1 | 2/2004 | Xu et al. |
| 2004/0064964 | A1 | 4/2004 | Lee |
| 2004/0118281 | A1 | 6/2004 | Leitch et al. |
| 2005/0229323 | A1 | 10/2005 | Mills et al. |
| 2007/0003432 | A1 | 1/2007 | Christensen et al. |
| 2007/0173403 | A1 | 7/2007 | Koike et al. |

OTHER PUBLICATIONS

United States Patent Trademark Office Action mailed Jul. 21, 2010, for U.S. Appl. No. 12/151,840, filed May 8, 2008, pp. 1-24.
Office Action dated Jun. 24, 2009, U.S. Appl. No. 12/151,840, filed May 8, 2008.
United States Patent and Trademark Office, Office Action, Mailed: Mar. 18, 2010, U.S. Appl. No. 12/151,840, filed May 8, 2008, First Named Inventor: Maximilian A. Biberger, 20 pages.
United States Patent and Trademark Office, Advisory Action, Mailed: May 27, 2010, U.S. Appl. No. 12/151,840, filed May 8, 2008, First Named Inventor: Maximilian A. Biberger, 3 pages.
Office Action dated May 4, 2009, U.S. Appl. No. 12/151,932, filed May 8, 2008.
Office Action from the United States Patent and Trademark Office, U.S. Appl. No. 12/151,840, filed May 8, 2008, First Named Inventor, Maximilian A. Biberger, Mail Date: Nov. 25, 2009.
Final Office Action mailed on Jan. 4, 2011, for U.S. Appl. No. 12/151,840, filed May 8, 2008, for Biberger et al.; 24 pages.
U.S. Appl. No. 12/151,805, filed May 8, 2008, for Biberger. (copy not attached).
White, A. et al. (2006). "Effective Terminal Sterilization Using Supercritical Carbon Dioxide," *Journal of Biotechnology* 123: 504-515.

* cited by examiner

*Primary Examiner* — Michael C. Wilson
(74) *Attorney, Agent, or Firm* — Morrison & Foerster LLP

(57) ABSTRACT

A method of introducing an additive to a biological material using a supercritical fluid is disclosed. The method comprises placing the biological material in a processing chamber, adding an additive to the supercritical fluid to form a supercritical fluid-additive mixture, adding the supercritical fluid-additive mixture to the processing chamber, and pulsing the mixture in the processing chamber. A processing system for introducing an additive to a biological material using a supercritical fluid in accordance with the present invention comprises a processing chamber for housing the biological material, a vat for storing a processing fluid, a pump, a heating element, an inlet port, and a flow path.

19 Claims, 4 Drawing Sheets ent of the present invention.

SYSTEM FOR AND METHOD OF INTRODUCING ADDITIVES TO BIOLOGICAL MATERIALS USING SUPERCRITICAL FLUIDS

RELATED APPLICATIONS

This application claims priority under 35 U.S.C. §119(e) to Provisional U.S. Patent Application No. 60/928,946 filed May 11, 2007 entitled "MATERIAL PRODUCTION SYSTEM AND METHOD" which are hereby incorporated by reference.

FIELD OF THE INVENTION

The present invention relates generally to the field of introducing additives to biological materials. More specifically, the present invention relates to a system for and a method of introducing additives to biological materials using supercritical fluids.

BACKGROUND OF THE INVENTION

There are occasions when biological materials, such as bone, skin, soft tissue, cartilage, muscle, and the like, lack desired biological and biomechanical properties. Oftentimes, such occasions arise due to circumstances, including but not limited to accidents, illnesses, diseases, genetic defects, unexpected mutations, and medical procedures (such as chemotherapy), as well as sterilization and processing methods.

One available solution is to treat a biological material with a highly concentrated additive solution, such that a portion of the additive will diffuse into the biological material. Additives include such items as proteins, lipids, cells, bone marrow, bone morphogenic proteins (BMPs), and stem cells, to name a few. Unfortunately, there are several deficiencies with conventional methods of treating with additives.

First, it is oftentimes difficult and sometimes impossible to successfully penetrate biological materials with additives using conventional infusion methods. For instance, some biological materials can successfully thwart infusion attempts due to their diminutive pores, membranes, matrices, or protective outer layers. Therefore, known techniques often culminate in the incomplete infusion of an additive. For example, it is known that treating the exterior of a bone material with a highly concentrated BMP solution will encourage bone growth. However, a very high concentration of the protein solution is needed to penetrate the bone material. Even so, the solution is only able to penetrate the bone at a small depth. Therefore, typical treatments result in the growth of bone material in a hollow shell due to the concentration's inability to penetrate into the interior of the bone. This is highly problematic.

Second, some conventional infusion methods require a complicated sequence of steps that include numerous processing chambers and multiple solvents, chemicals and reagents, thereby increasing the costs associated with an infusion and making the process labor-intensive and prone to error.

Third, some conventional methods are not clean nor environmentally friendly. Instead, conventional methods use toxic solvents, chemicals and reagents, which may contaminate biological materials with undesirable residues and taints. In fact, certain solvents used with traditional methods of treating biological materials are prohibited from use in certain countries.

BRIEF SUMMARY OF THE DISCLOSURE

In accordance with the present invention, a method of introducing an additive to a biological material using a supercritical fluid is disclosed. In the preferred embodiment, four process steps are utilized to introduce additive to a biological material. In the first step, the biological material is placed in a processing chamber. In the second step, an additive is added to a supercritical fluid, thereby forming a first additive chemistry. In the third step, the first additive chemistry is added to the processing chamber. In the fourth step, the first additive chemistry is pulsed in the processing chamber. Pulsing causes the infusion of the mixture into the biological material, and eventually, the supercritical fluid separates from the additive, leaving the additive in the biological material. All these steps are performed in situ in the processing chamber. The steps can be performed automatically, thus, dramatically reducing labor costs.

The present invention also includes a processing system for introducing an additive to a biological material using a supercritical fluid. The processing system comprises a processing chamber, a vat, a pump, a heating element, an inlet port, and a flow path. The processing chamber houses the biological material to be processed. The vat is coupled to the processing chamber through a flow path. In operation of the system, a supercritical fluid flows through the flow path from the vat to the processing chamber. An additive is added to the supercritical fluid to form a first additive chemistry. Preferably, the additive is added to the supercritical fluid before the supercritical fluid enters the flow path. Once the supercritical fluid-additive mixture successfully enters the processing chamber, the mixture is infused into the biological material through pulsing. The supercritical fluid in the mixture can thus fluctuate from its supercritical and nonsupercritical states based on the effects of the pulsing due to changes in temperature and pressure. During the pulsing, the supercritical fluid separates from the additive, leaving the additive in the biological material. Optionally, the processing system can include a recirculation loop which allows the supercritical fluid to exit the processing chamber and later be recycled back into the processing chamber.

DETAILED DESCRIPTION OF THE PRESENT INVENTION

The present invention discloses a method of and a system for introducing an additive into a biological material using a supercritical fluid, such as supercritical CO2. Supercritical fluids have efficient infusion and deep penetration capabilities. Furthermore, supercritical fluids are superior to most chemicals, solvents and reagents used in conventional infusion methods, because supercritical fluids can deeply infuse biological materials like a gas and dissolve undesirable substances like a liquid. Furthermore, supercritical fluid infusion and processing can be controlled by adjusting certain variables, such as pressure and temperature, so that additives can easily penetrate the biological material, but without the use of harsh chemicals, reagents or solvents. Also, the present invention allows for infusion of biological materials without disrupting their structural integrity and without destroying the biological and biomechanical properties of such biological materials.

Figure 1:
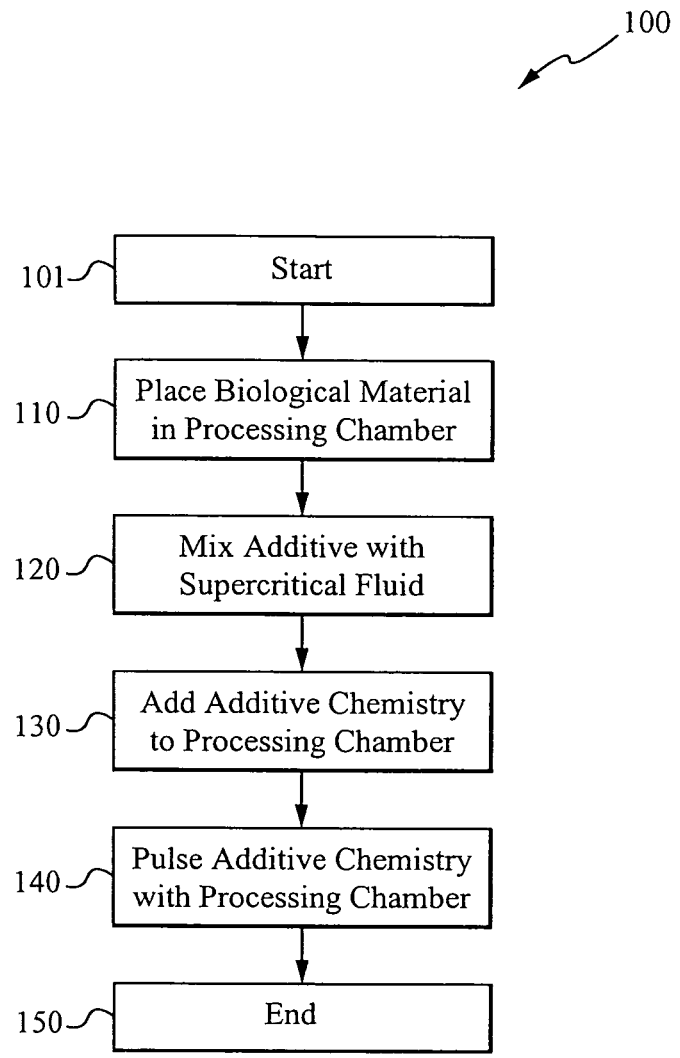
FIG. 1 is a flow chart illustrating a processing sequence of steps for introducing an additive to a biological material using a supercritical fluid, in accordance with a preferred embodiment of the present invention.

FIG. 1 illustrates a processing sequence 100 for introducing an additive to a biological material in accordance with the preferred embodiment of the invention. At the start step 101, the biological material is provided. "Biological material" as defined in this invention is any material that is a part of or intended for a living system, or any material that functions with living cells or tissue. Biological material can be natural, synthetic, or a combination of both. It can be used to replace or augment a part of a living system. Biological materials include but are not limited to bone, skin, soft tissue, muscular tissue, cells, stem cells, biomaterials, and grafting materials. In some embodiments of the present invention autografts are provided. In other embodiments of the present invention, allografts, isografts, or xenografts are provided. In the preferred embodiment, the bone material is an allograft, from a human donor or a cadaver, intended for implantation into a human host.

At the step 110, the biological material to be processed is placed in a processing chamber. At the step 120, the additive is mixed with the supercritical fluid, thereby forming an additive chemistry. Preferably, the supercritical fluid is supercritical $CO_2$. Next, at the step 130, the additive chemistry is delivered to the processing chamber which houses the biological material. Then, at the step 140, the additive chemistry inside the processing chamber undergoes "pulsing".

It will be apparent to one skilled in the art that the term "pulsing," as set forth in the present invention and specifically in the step 140, refers to the fluctuation of the supercritical fluid in the mixture, such that the supercritical fluid fluctuates between its nonsupercritical state and its supercritical state. This can be done any number of ways. Preferably, this is done through fluctuating the pressure of the mixture. Alternatively, pulsing can occur from a first supercritical pressure and a second supercritical pressure. Alternatively, pulsing is done through fluctuating the temperature of the mixture, or fluctuating both the temperature and the pressure of the mixture. In the preferred embodiment of the present invention, pulsing is achieved by fluctuating the pressure of the supercritical fluid.

As stated previously, in the preferred embodiment, CO2 is the supercritical fluid in the mixture. It is well known that CO2 reaches its supercritical state when the temperature is above 30.5 degrees Centigrade and the pressure is above 1070.4 psi. As a result of the pressure and/or temperature fluctuations of the additive chemistry, at the step 140, the mixture deeply penetrates and infuses the biological material and supercritical fluid in the mixture fluctuates from its supercritical and nonsupercritical states. During this pulsing, the supercritical fluid cleanly separates from the additive, thereby leaving the additive inside the biological material. Finally, at the step 150, the processing of the biological material is completed.

One advantage of the present invention lies in the ability of the supercritical fluid-additive mixture to deeply penetrate the biological material, particularly in those cases where the additive (by itself or with the help of multiple reagents, chemicals and solvents) cannot successfully infuse the biological material. This alone presents clear advantages over the current practices in the biological processing art.

Furthermore, a second advantage is that the present invention allows for the infusion of the additive into the biological material without disturbing or harming the biological material's innate properties, including the structural integrity of the biological material. For example, known techniques of pre-processing biological material involves using chemicals which damage or kill biological material growth factors.

Yet another advantage is that the entire processing method can be accomplished within one single chamber, and thus requires little, if any, handling or transferring of the biological material. Finally, the supercritical fluid during pulsing cleanly separates from the additive, allowing the additive to remain in the biological material without leaving a harmful residue.

Figure 2:
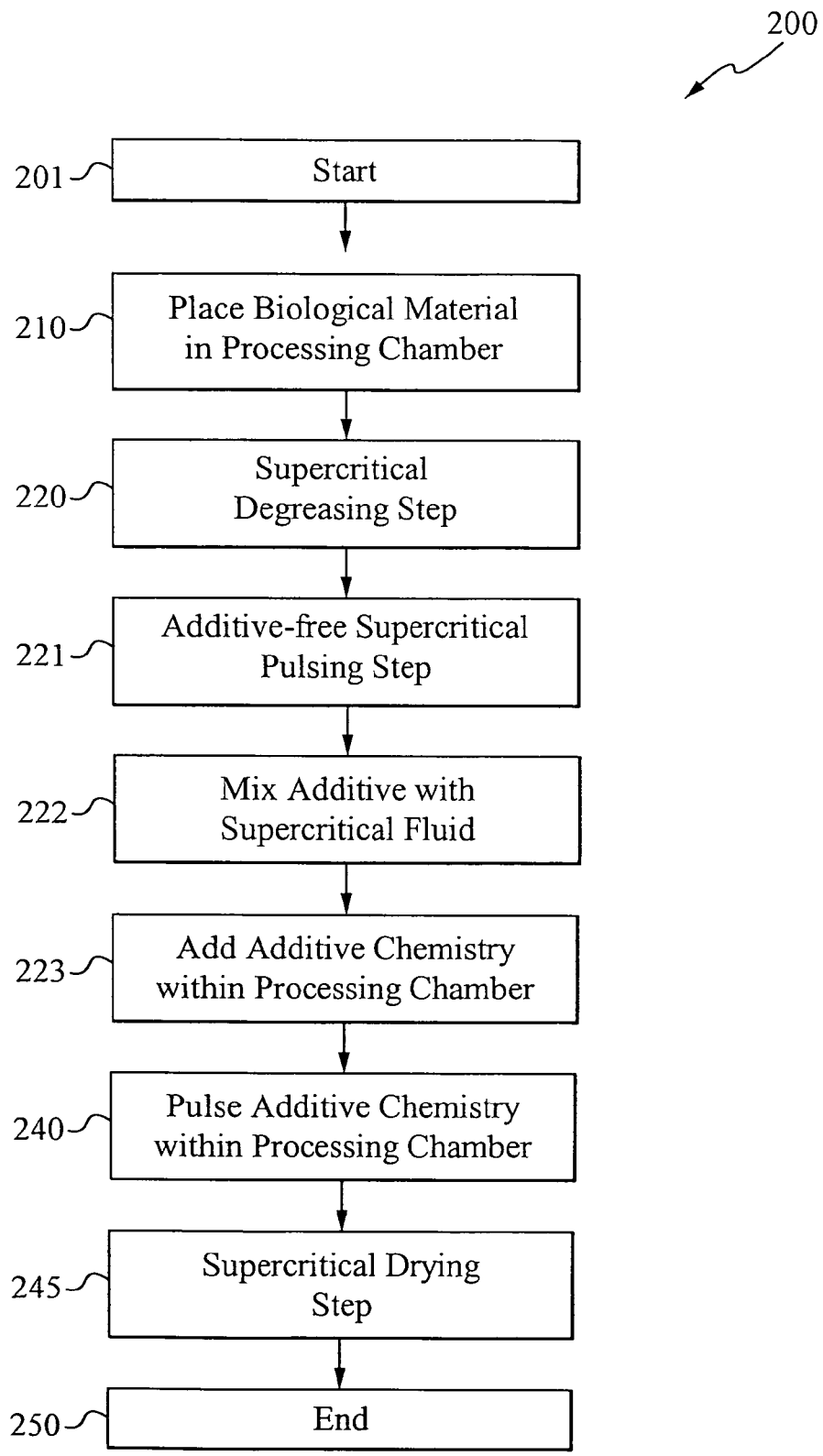
FIG. 2 is a flow chart illustrating a processing sequence of steps for pre-processing a biological material using a supercritical degreasing chemistry, introducing an additive to a biological material using a supercritical fluid and drying the material using a supercritical drying chemistry in accordance with some embodiments of the present invention.

In alternative embodiments of the present invention, the biological material is pre-processed, infused with an additive and dried using supercritical fluids. FIG. 2 illustrates this alternative processing sequence 200 for introducing an additive to a biological material in accordance with some embodiments of the present invention.

At the start step 201, biological material is provided. At the step 210, the biological material to be processed is placed in a processing chamber. In the preferred embodiment of the present invention, a single processing chamber is used throughout the processing sequence 200.

Next, a supercritical degreasing step 220 is performed. The degreasing step 220 involves delivering a supercritical fluid along with a degreasing chemistry to the processing chamber that holds the bone material. The degreasing chemistry aides in bone degreasing and in extracting liquids from the bone matrix. Preferably, the supercritical fluid is supercritical $CO_2$ and the degreasing chemistry is an alcohol, such as acetone. It is well known that $CO_2$ reaches its supercritical state when the temperature is above 30.5 degrees Centigrade and the pressure is above 1070.4 psi. The degreasing step 220 concludes with flushing the supercritical fluid and degreasing chemistry from the processing chamber.

Next, an additive-free supercritical pulsing step 221 is performed. The additive-free supercritical pulsing step involves delivering substantially pure supercritical fluid to the processing chamber and pulsating the fluid. Preferably, the supercritical fluid is supercritical $CO_2$. The additive-free pulsing of the supercritical fluid inside the processing chamber involves fluctuating the pressure of the supercritical fluid, fluctuating the temperature of the supercritical fluid, or a combination thereof. Pulsing the additive-free supercritical fluid is performed to kill and extract contaminants, such as bacteria, donor cells, viruses, and the like which are present within the bone material.

In some embodiments of the present invention, supercritical $CO_2$ fluctuates in a cycle from its supercritical state to its nonsupercritical state, through the varying ranges of pressure and temperature. Alternatively, additive-free pulsing can occur from a first supercritical pressure and a second supercritical pressure. However, it will be readily apparent to those having ordinary skill in the relevant art that a number of temperature and pressure fluctuations may be used to kill the contaminants present in the bone material.

The destruction of the contaminants occurs as the supercritical fluid infuses into the undesirable contaminants. Once infused into the contaminants, the step of additive-free pulsing pressure and temperature cause the membranes of the contaminants to explode or implode. In a preferred embodiment, the additive-free pulsing step is rapid, which in turn causes the supercritical fluid to disrupt, lyse and crack the walls of bacteria, viruses, donor cells, and the like. The additive-free supercritical pulsing step present clear advantages over the bacteria killing step practiced in the prior art because, unlike the use of an oxidizer to eliminate contaminants and a base chemistry to remove proteins, using the additive-free supercritical pulsing step eliminates unwanted contaminants, but does not destroy collagen, Bone Morphogenetic Proteins (BMPs), or other growth factors.

An additional benefit of the additive-free supercritical pulsing step 221 includes agitating contaminants present within the bone matrix, causing the contaminants to be removed from the bone matrix. In addition to killing contaminants, it is also beneficial to the osteoconductive and osteoinductive processes to remove dead contaminants from the bone matrix.

Another benefit of the additive-free supercritical pulsing step 221 lies in the ability of supercritical fluid to destroy prions. Prions are misshapen proteins typically found in fat that are thought to be linked with neurodegenerative diseases, such as mad cow disease, fatal familial insomnia, Gerstmann-Straussler syndrome, and Creutzfeldt-Jakob disease, to name a few. Prions are extremely difficult to kill, and under conventional method, strong oxidizers are used to accomplish this task. However, strong oxidizers in the conventional method can be advantageously replaced by supercritical fluids in the present invention, since supercritical fluids also eliminate prions. Thus, the use of supercritical fluid as an extractor of contaminants, including prions, at the step 221 (FIG. 2) in accordance with the present invention, prevents the transfer of diseases from the donor to the host via a bone transplant, without the disadvantage of using a multitude of strong, sometimes toxic chemicals.

The additive-free supercritical pulsing step 221 ends with flushing the fluid and the contaminants from the processing chamber. In some embodiments of the present invention a recirculation loop system is utilized to reuse supercritical fluid after the contaminants and the supercritical fluid exit the processing chamber. In some embodiments of the present invention, the contaminants are filtered out from the supercritical fluid using a filter, and the remaining supercritical fluid reenters the processing chamber through a loop, for the supercritical fluid to be reused for another next cycle.

In an alternative embodiment, the supercritical fluid enters the processing chamber through a flow path. Through pulsing, the supercritical fluid extracts the contaminants, which separate from biological material without a filter or a recirculation loop. For instance, contaminants can separate from biological material through condensation, preferably in one processing chamber. Those skilled in the art will also recognize other processes for separating contaminants from bone material, without using filtration or recirculation systems.

At the step 222, the additive is mixed with the supercritical fluid, thereby forming an additive chemistry. Preferably, the supercritical fluid is supercritical $CO_2$. Next, at the step 223, the additive chemistry is delivered to the processing chamber which houses the biological material. Then, at the step 240, the additive chemistry inside the processing chamber undergoes "pulsing", as explained above.

Next, at the step 245, the biological material is dried using supercritical fluid and a drying chemistry. In some embodiments of the present invention, a combination of supercritical $CO_2$ and alcohol is used for the proper rinsing of the bone material. In some embodiments of the present invention, acetone is used as the drying chemistry. The use of the supercritical drying step presents clear advantages over the prior art because using supercritical fluid for the delivery of the drying chemistry allows the drying agent to more-fully permeate the bone matrix to remove unwanted moisture. This step of drying is important due to the adverse effects of left over moisture with the bone matrix such as the prevention of cell migration through the structure (resulting in a decreased osteoconductivity) and the cracking of the bone structure as the biological material is cooled down to preserve the graft, among other negative effects. Finally, at the step 250, the biological material is ready to be implanted into the host's body.

The processes illustrated in FIG. 1 and FIG. 2 are a preferred embodiment and one alternative embodiment of the present invention. However, it will be clear to those having ordinary skill in the art that any number of processing techniques or sequences may benefit from pulsing an additive chemistry, as taught within this disclosure, within a processing chamber to infuse the contents with the additive. For example, in some embodiments of the present invention, following the application of the rinsing agents, gamma radiation can also be applied to the biological material.

Figure 3:
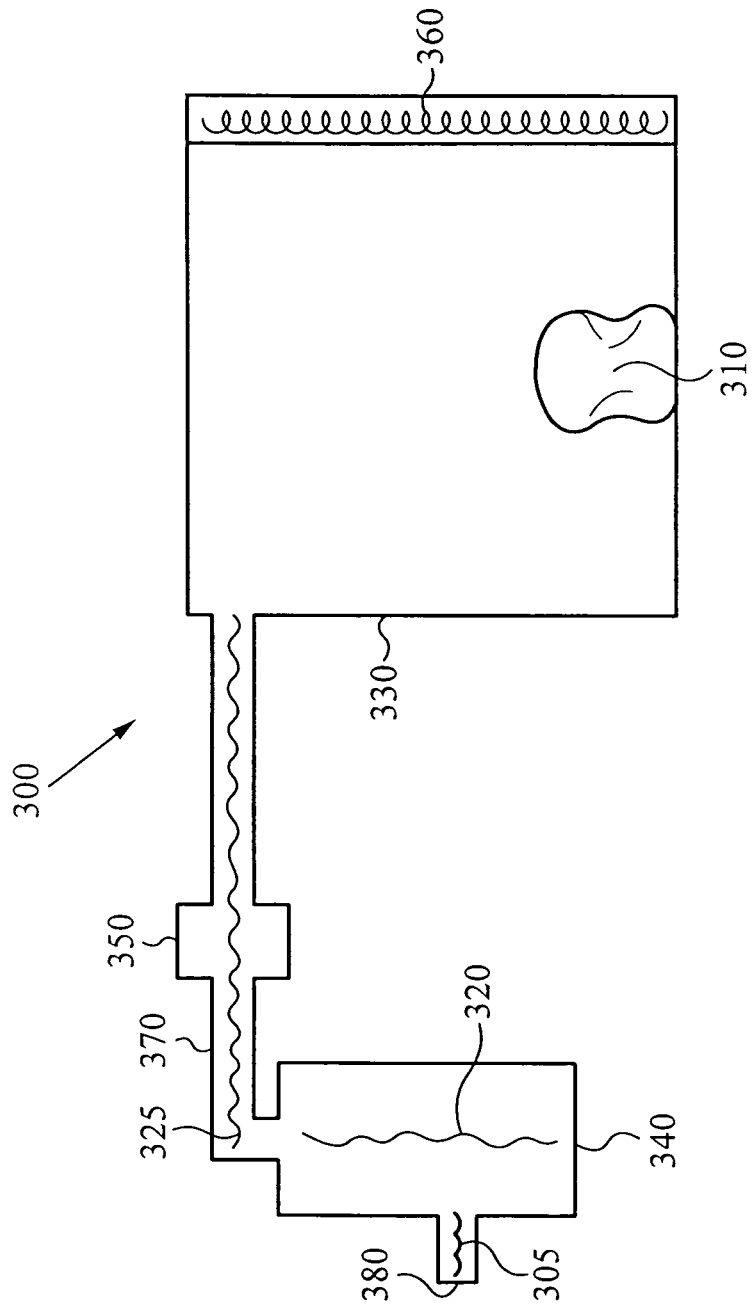
FIG. 3 is a block diagram illustrating a processing system for introducing an additive to a biological material using a supercritical fluid, in accordance with the preferred embodiment of the present invention.

FIG. 3 illustrates a processing system 300 for introducing an additive 305 to a biological material 310 using a processing fluid 320, in accordance with the preferred embodiment. Preferably, the processing fluid 320 is supercritical CO2. The processing system 300 comprises a processing chamber 330, a vat 340, a pump 350, a heating element 360, a flow path 370, and an inlet port 380. The processing chamber 330 is coupled to the vat 340 through the flow path 370. The pump 350 and the heating element 360 are coupled to the processing chamber 330. Preferably, the pump 350 is coupled to the flow path 370, which eventually leads to the processing chamber 330. Preferably, the heating element 360 is outside the processing chamber 330.

Initially, the processing chamber 330 houses the biological material 310 to be processed. In the preferred embodiment, the biological material 310 is an allograft from a human donor intended for a human host. However, it will be apparent to those skilled in the art that the present invention can also be used in autografts and xenografts alike. While FIG. 3 illustrates a processing system 300 having a single processing chamber 330, it will be apparent to those skilled in the art that the processing system 300 can comprise any number of processing chambers for performing multiple processes on a biological material or for concurrently processing multiple biological materials.

The processing fluid 320 initially is inside the vat 340. The vat 340 is coupled to the processing chamber 330 through a flow path 370. In operation, once the processing of the biological material 310 begins, the additive 305 is added to the processing fluid 320 through an inlet port 380, thereby forming an additive chemistry 325. Preferably, the inlet port 380 is coupled to the vat 340. However, the inlet port 380 can be located anywhere throughout the processing system 300. Further, the additive 305 can be added to the processing fluid 320 at any stage during the processing of the biological material 310.

In the preferred embodiment, the additive chemistry 325 flows from the vat 340 through the flow path 370 and into the processing chamber 330. Once the additive chemistry 325 successfully enters the processing chamber 330, the mixture 325 undergoes pulsing to begin the infusion process of the additive chemistry 325 into the biological material 310.

The term "pulsing" in reference to the processing system 300 refers to the fluctuation of the processing fluid 320 in the additive chemistry 325, such that the processing fluid 320 fluctuates between its nonsupercritical state and its supercritical state. This can be done any number of ways. Preferably, this is done through fluctuating the pressure of the mixture 325 with the help of the pump 360. Alternatively, pulsing can occur from a first supercritical pressure and a second supercritical pressure. Alternatively, pulsing is done through fluctuating the temperature of the additive chemistry 325 with the help of the heating element 360, or fluctuating both the temperature and the pressure of the additive chemistry 325 using both the pump 360 and the heating element 360. It will be apparent to those skilled in the art how the processing fluid 320 in the additive chemistry 325 can be cooled at times to reach its non-supercritical state. For instance, the processing chamber 330 can be opened at certain times or a refrigerant agent can be added to the processing system 300 to lower the temperature of the processing fluid 320.

In the preferred embodiment, the additive chemistry 325 infuses into the biological material 310 and during pulsing, the processing fluid 320 separates from the processing additive chemistry 325, thereby leaving the additive 305 in the biological material 310. Finally, the processing of the biological material 310 is completed. After its processing through the processing system 300, the final product is a biological material 310 that retains its biomechanical and biological properties and which now comprises the additive 305. Preferably, the additive 305 adds, augments, or enhances a biological or biomechanical property of the biological material 310.

An example of such an additive 305 is bone morphogenic proteins (BMPs), which are growth factors key to bone osteoconductivity and osteoinductivity. Conventionally, BMPs are difficult to infuse into bone, particularly human bone grafts, and even when conventional methods are able to infuse BMPs into bone, these methods do not successfully trigger natural cell proliferation. Instead, conventional infusion methods of BMPs into bone grafts eventually result in defective, hollowed bone grafts with abnormal cell proliferation. Using the present invention, with the aid of supercritical fluid as a processing fluid 320, BMPs can successfully infuse in bone with little or no difficulty, without harming the native properties of the bone, and can advantageously help in the natural bone cell rebuilding and regeneration.

It will be readily apparent to one skilled in the art that various modifications may be made to the embodiments without departing from the spirit and scope of the invention. For instance, a recirculation loop, additional chemistry vats, or the like can be optionally added to the processing system.

Figure 4:
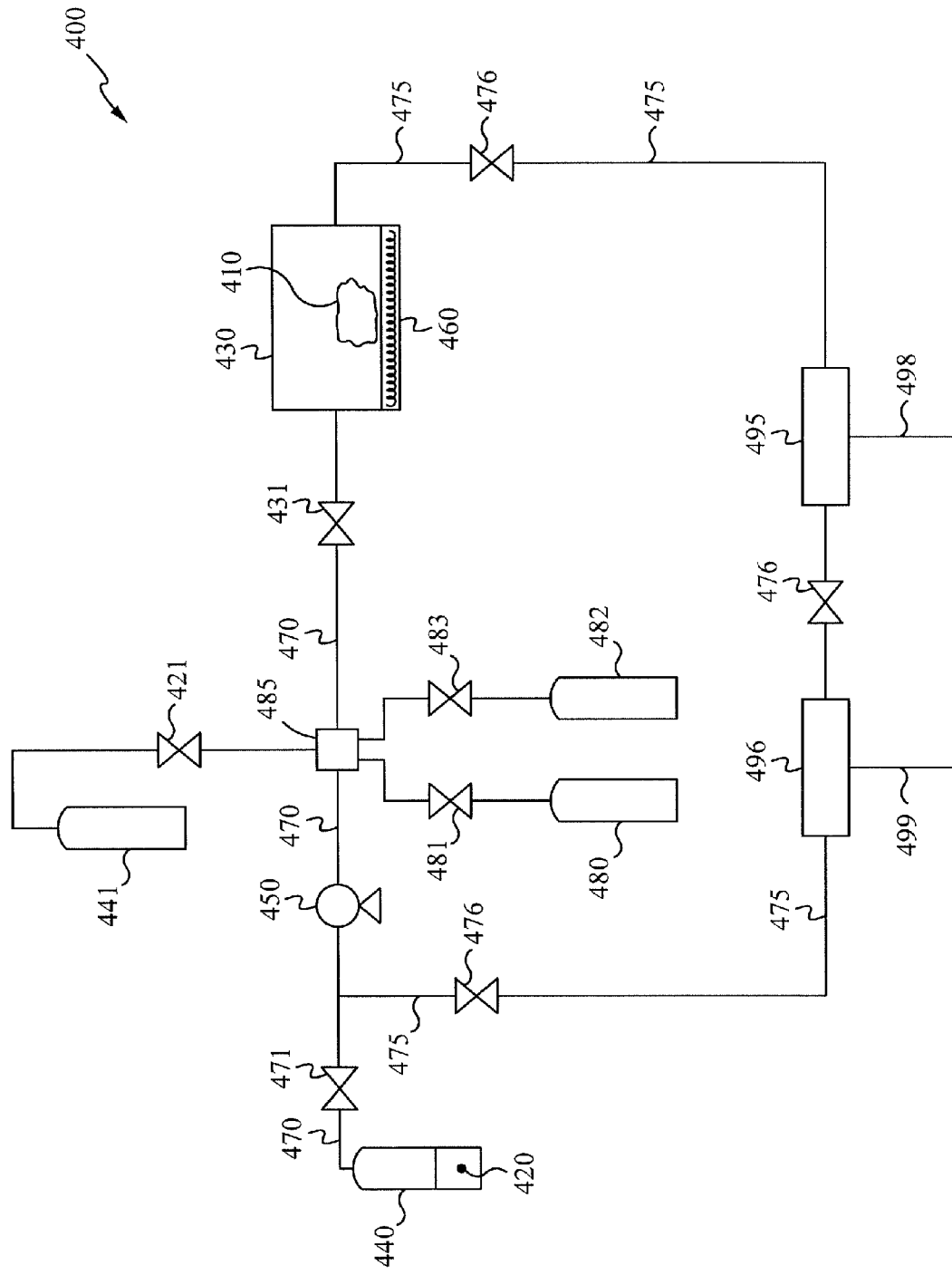
FIG. 4 is a block diagram illustrating an alternative processing system utilizing a recirculation loop according to some embodiments of the present invention.

FIG. 4 illustrates a processing system 400 for processing biological material 410 using a processing fluid 420 in accordance with some embodiments of the present invention. The processing system 400 comprises a processing chamber 430, a vat 440, a pump 450, a flow path 470, a valve 471, an additive tank 441, a first chemistry tank 480, a second chemistry tank 482, a mixer 485, a recirculation loop 475, and components 495 and 496.

As shown in FIG. 4, the vat 440, the additive tank 441, the first chemistry tank 480 and the second chemistry tank 482 (collectively "tanks") are coupled to the mixer 485. Valves 421, 481, and 483 are provided between the tanks and the mixer 485 to optionally ensure that fluid delivered to the mixer 485 from the tanks possesses some prerequisite pressure. In some embodiments of the present invention, heaters (not shown) heat the chemistry contained within the tanks to heat the chemistries to some prerequisite temperature.

The mixer 485 is configured to receive and mix processing fluid 420 from the vat 440 and one or more chemistries from the tanks. In some embodiments of the present invention, a degreasing chemistry from tank 480 is mixed with the processing chemistry 420 to carry out a degreasing step, an additive from tank 441 is mixed with the processing chemistry 420 to carry out an additive pulsing step, and a drying chemistry from tank 482 is mixed with the processing chemistry 420 to carry out a supercritical drying step.

Mixed fluid is delivered via the flow path 470 to the processing chamber 430. A valve 431 is positioned between the mixer 485 and the processing chamber 430 to optionally ensure that fluid delivered from the mixer 485 to the processing chamber 430 possesses some prerequisite pressure. In some embodiments of the present invention, the valve 431 is dynamically controllable to vary the pressure of the fluid delivered to the processing chamber in order to accomplish the pulsing step, as explained above. Likewise, a heating element 460 is coupled to the processing chamber 430 and the heating element 460 is dynamically controllable to vary the temperature of the fluid delivered to the processing chamber in order to accomplish the pulsing step, as explained above.

According to FIG. 4, the fluid in the processing chamber 430 exits the processing chamber 430 into a recirculation loop 475. A number of valves 476 are positioned within the recirculation loop 475 to control pressure. Also contained within the recirculation loop 475 are components 495 and 496. Components 495 and 496 can include, but are not limited to separator, filters or the like. In some embodiments of the present invention, outlet lines 498 and 499 are coupled to the components 495 and 496, respectively.

In some embodiments of the present invention, contaminants are filtered out from the processing fluid, leaving remaining fluid. The recirculation loop 475 is configured such that the remaining fluid reenters the flow path 470 to be reused for the next processing cycle. Any number of cycles and types of filters necessary to extract undesirable contaminants of bone material can be used, based on the application at hand.

Reference has been made in detail to the preferred and alternative embodiments of the invention, examples of which are illustrated in the accompanying drawings. While the invention has been described in conjunction with the preferred embodiments, it will be understood that they are not intended to limit the invention to these embodiments. On the contrary, the invention is intended to cover alternatives, modifications and equivalents, which may be included within the spirit and scope of the invention. Furthermore, in the detailed description of the present invention, numerous specific details have been set forth in order to provide a thorough understanding of the present invention. However, it should be noted that the present invention may be practiced without these specific details. In other instances, well known methods, procedures and components have not been described in detail as not to unnecessarily obscure aspects of the present invention.

The invention claimed is:

1. A method of infusing a protein into bone material comprising:
   a) introducing bone material into a processing chamber;
   b) introducing a mixture of a supercritical fluid and the protein into the processing chamber; and
   c) performing a pulsing step on the mixture such that the supercritical fluid fluctuates between its nonsupercritical state and its supercritical state, wherein some of the protein is infused into the bone material and some remains in the supercritical fluid, thereby forming an infused bone material comprising a portion of the protein.

2. The method of claim 1, further comprising:
removing the fluid comprising a remaining portion of the protein from the processing chamber;
directing the fluid comprising the remaining portion of the protein into a recirculation loop; and
processing the fluid comprising the remaining portion of the protein, forming recycled fluid.

3. The method of claim 2, further comprising:
recirculating the recycled fluid into the processing chamber.

4. The method of claim 2, further comprising:
recirculating the recycled fluid into at least one additional processing chamber.

5. The method of claim 2, wherein processing comprises filtering the fluid comprising the remaining portion of the protein with a filter.

6. The method of claim 2, wherein processing comprises separating out the protein present in the fluid comprising the remaining portion of the protein with a separator.

7. The method of claim 1, wherein the bone material is bone harvested from a human donor.

8. The method of claim 1, wherein the bone material is bone harvested from an animal donor.

9. The method of claim 1, wherein the fluid is supercritical $CO_2$.

10. The method of claim 1, wherein the pulsing step comprises:
fluctuating the pressure of the mixture causing the fluid to fluctuate between supercritical and non-supercritical states, thereby infusing the portion of the protein into the bone material.

11. The method of claim 1, wherein the pulsing step comprises:
fluctuating the temperature of the mixture causing the fluid to fluctuate between supercritical and non-supercritical states, thereby infusing the portion of the protein into the bone material.

12. The method of claim 1, wherein the pulsing step comprises:
fluctuating the temperature and the pressure of the mixture causing the fluid to fluctuate between supercritical and non-supercritical states, thereby infusing the portion of the protein into the bone material.

13. The method of claim 1, further comprising:
a. introducing a degreasing chemistry into the processing chamber before the pulsing step, wherein the degreasing chemistry comprises a supercritical fluid and a degreasing agent.

14. The method of claim 13, wherein the drying agent is acetone.

15. The method of claim 1, further comprising:
a. introducing a substantially additive-free supercritical fluid into the processing chamber before the pulsing step; and
b. performing additive-free pulsing step on the substantially additive-free supercritical fluid, wherein the additive-free pulsing step kills substantially all the contaminants present within the bone material, forming dead contaminants.

16. The method of claim 15, wherein the additive-free pulsing step agitates the dead contaminants present in the bone material, thereby removing the dead contaminants from the bone material.

17. The method of claim 1, further comprising:
a. introducing a drying chemistry into the processing chamber after the pulsing step, wherein the drying chemistry comprises a supercritical fluid and a drying agent.

18. The method of claim 1, further comprising:
exposing the bone material to gamma-ray radiation.

19. The method of claim 1, wherein the protein is a bone morphogenic protein.

* * * * *